US005667797A

United States Patent [19]

Peterson et al.

[11] Patent Number: 5,667,797
[45] Date of Patent: *Sep. 16, 1997

[54] ANTI-VIRAL COMPOSITION AND KIT AND USE FOR TREATING ROTAVIRUS INFECTION AND DIARRHEA

[75] Inventors: Jerry A. Peterson, Lafayette, Calif.; David S. Newburg, Newtonville, Mass.; Robert H. Yolken, Baltimore, Md.

[73] Assignees: Cancer Research Fund of Contra Costa; Senomed, Inc., both of Walnut Creek, Calif.; The Johns Hopkins University School of Medicine, Baltimore, Md.

[*] Notice: The term of this patent shall not extend beyond the expiration date of Pat. No. 5,505,959.

[21] Appl. No.: 626,057

[22] Filed: Apr. 1, 1996

Related U.S. Application Data

[63] Continuation of Ser. No. 378,865, Jan. 23, 1995, Pat. No. 5,505,955, which is a continuation of Ser. No. 969,949, Oct. 30, 1992, abandoned.

[51] Int. Cl.$^6$ .................................................. A61K 45/00
[52] U.S. Cl. ........................... 424/439; 424/440; 424/441; 424/451; 424/464; 424/484; 424/535; 424/85.4; 424/94.1; 424/208.1; 424/215.1; 514/2; 514/904; 514/905; 514/867; 514/937; 514/962; 514/8
[58] Field of Search .................... 424/439, 440, 424/441, 484, 451, 464, 535, 84.4, 30.1, 94.1, 208.1; 514/867, 2, 904, 905, 937, 962; 426/657

[56] References Cited

U.S. PATENT DOCUMENTS

| | | | |
|---|---|---|---|
| 4,401,657 | 8/1983 | Kashiwabara et al. | 424/439 |
| 5,053,406 | 10/1991 | Smka et al. | 514/182 |
| 5,143,727 | 9/1992 | Ebina | 424/89 |
| 5,230,912 | 7/1993 | Yajima et al. | 426/43 |

FOREIGN PATENT DOCUMENTS

| | | |
|---|---|---|
| 391416 | 10/1990 | European Pat. Off. |
| 8806035 | 2/1988 | WIPO |

OTHER PUBLICATIONS

Taniguchi, et al., "Process for preparing a therapeutic agent from milk for rotavirus infection and pharmaceutical granules containing the same," CA114(22):21443t (1990).

Yolken, et al., "Human Milk Mucin Inhibits Rotavirus Replication and Prevents Experimental Gastroenteritis," J. Clin. Invest., vol. 90:1984–1991 (Nov. 1992).

Larocca, et al., "Cloning and Sequencing of a Complementary DNA Encoding a $M_r$ 70,000 Human Breast Epithelial Mucin–associated Antigen," *Cancer Research* 50:5925–5930 (1990).

Larocca, et al., "A $M_r$ 46,000 Human Milk Fat Globule Protein That Is Highly Expressed in Human Breast Tumors Contains Factor VIII–like Domains," *Cancer Research* 51:4994–4998 (1991).

*Primary Examiner*—Raj Bawa
*Attorney, Agent, or Firm*—Viviana Amzel; Pretty, Schroeder & Poplawski

[57] ABSTRACT

An anti-diarrheic product comprises a foodstuff and an anti-rotaviral agent such as human defatted fat globule membranes, the human milk macromolecular fraction, skim milk, curd, whey, the milk mucin complex, the 46 Kd app.MW glycoprotein, a polypeptide having an amino acid sequence having the rotavirus binding specificity of the 46 Kd app.MW HMFG glycoprotein or mixtures thereof. An anti-diarrheal kit comprises the anti-rotaviral agent of this invention and instructions for its use, and optionally a foodstuff. A method for inhibiting or countering rotavirus infection in mammalian cells comprises contacting the cells with an anti-rotaviral amount of the agent of this invention. A therapeutic method for inhibiting the onset of or countering rotavirus infection comprises administering to a subject afflicted with or at risk for rotavirus infections such as those occuring, for example, in infants and children (infantile gasteroenteritis) and immunodeficient persons or those who have received a transplant, an anti-rotaviral effective amount of the agent of this invention.

63 Claims, No Drawings

ANTI-VIRAL COMPOSITION AND KIT AND USE FOR TREATING ROTAVIRUS INFECTION AND DIARRHEA

This application is a continuation of U.S. patent application Ser. No. 08/378,865, filed Jan. 23, 1995, which issued as U.S. Pat. No. 5,505,955, which is a continuation of U.S. Ser. No. 07/969,949, filed Oct. 30, 1992 by the same inventors, now abandoned.

This invention was made with at least partial Government funding under Grant Nos. R01 DK 33089, CA 39932, CA 42767 HD 13021 from the National Institutes of Health. The United States government may have rights in this invention.

BACKGROUND OF THE INVENTION

1. Field of the Invention

This invention relates to a prophylactic and therapeutic composition for inhibiting rotavirus infection, and more particularly to a method of preventing and treating diseases or conditions associated with, or requiring, rotavirus infection, using defatted human milk globules (HMFGs), milk macromolecular fraction, curd, whey, the human milk mucin complex or a polypeptide having the rotavirus-binding specificity of the 46 Kdalton (Kd) app.MW HMFG glycoprotein. The present method finds its application in the prevention and treatment of diseases such as infantile gastroenteritis, and diarrheal conditions that afflict immunodeficient patients, the elderly and travelers.

2. Description of the Background

Gastroenteritis and diarrhea have been linked to rotavirus infection in a variety of clinical settings. In many cases the population afflicted by these diseases are the very young, the elderly and the immunocompromised. Acute infectious gastrointestinal diseases, for example, are a major cause of illness and death in infants and young children throughout the world. In the developing countries, infectious gastrointestinal diseases are estimated to cause up to 12,000 deaths per day. Diarrheal disease is also an important health problem in the developed countries. In the U.S., over 200,000 children under 5 years of age are hospitalized each year with acute diarrheal disease. This results in nearly 880,000 in-patient hospital days, over 500 deaths, and almost one billion dollars of in-patient costs per year.

Although various viral, bacterial, and parasitic agents are suspected of causing acute infectious gastroenteritis, rotaviruses have been identified as the most important viral agent of gastroenteritis, e.g., in children living in both developed and developing countries. Prospective studies indicate that in the U.S. rotaviruses account for around 2.9 million yearly episodes of diarrhea leading to 22,000 annual hospitalizations of children less than 5 years old. Rotaviruses have also been implicated as the causative agent of diarrheal outbreaks occurring in nursing homes, day care centers and during travel, and resulting from adult contacts with sick children. Additionally, rotaviruses have been linked with the occurrence of diarrhea in patients undergoing bone marrow transplants and suffering from various immunodeficient conditions.

Throughout history, breast-feeding infants were shown to be somewhat protected against enteric infection by pathogens in general when compared with bottle fed infants. In addition, breast-feeding was also shown to lower the incidence of enteric diseases, such as necrotizing enterocolitis of infancy, which may be infectious in origin but which have not been associated with a single etiologic agent. More recently, studies of children living in developing as well as developed countries such as Great Britain and the U.S. have shown that breast-fed infants undergo substantially fewer episodes of gastroenteritis than bottle-fed infants. In some studies breast-feeding was shown to lessen the severity of diarrhea and vomiting associated with rotavirus infection in hospitalized children, but not to provide total protection against infection in general, and serious episodes of rotavirus infection in particular. However, no single factor was found to be responsible for this effect in spite of the fact that antibodies were suspected of being involved in the effect. The level of anti-rotavirus antibody in human milk was found not to correlate with the degree of protection afforded by the milk. This suggested that non-immunoglobulin factors may play a role in the protective process. Among the non-immunoglobulin factors that have been implicated in this phenomenon are lipids, α-interferon and trypsin inhibitors, among others. It has also been suggested that some of these substances are possible inhibitors of viral replication and of microorganisms in general. A factor isolated from a milk fraction free of fat and cells was shown to inhibit the infectivity of respiratory syncytial virus (RSV). The factor has a molecular weight greater than 400 Kd app.MW, and is distinct from the present agents.

The growth of rotavirus and its infectivity were studied in various systems. Rotavirus replication was shown recently to be inhibited by avian egg and bovine submaxillary gland glycoproteins in cell culture. These glycoproteins bind to the virus and their activity requires sialic acid and proceeds by interference with the binding of the virus to cellular receptors. Intestinal brush border membranes were also shown to bind rotavirus by attachment to glycoproteins.

Human milk fat globules (HMFG) are obtained from the cream fractions of milk, and have been utilized to prepare polyclonal and monoclonal antibodies for use in the diagnosis of breast cancer. Both, anti-HMFG and anti-breast tumor monoclonal antibodies with specificities for different epitopes of the mucin complex have been produced. The anti-HMFG monoclonal antibodies were used to identify a large molecular weight mucin-like complex called non-penetrating glycoprotein (NPGP) on the surface of breast epithelial The human milk mucin is a highly glycosylated macromolecular complex consisting of 50% carbohydrate, most of which is O-linked in addition to the mucin molecule, this complex contains a disulfide-linked 70 Kd apparent molecular weight (app.MW) glycoprotein and a 46 Kd app.MW glycoprotein. Monoclonal antibodies raised against the 70 Kd app.MW and 46 Kd app.MW glycoproteins have also been produced. The 46 Kd app.MW and 70 Kd app.MW glycoproteins are found in the serum of breast cancer patients and may thus be used as markers for breast cancer. The 70 Kd app.MW glycoprotein, in particular, was found to co-purify with the intact mucin complex and to be linked to the mucin complex through disulfide bonds, making it a suspect linker protein of this complex on the breast epithelial surface.

The structure of the polypeptide associated with the 70 Kd app.MW glycoprotein was determined by, cDNA cloning. A partial amino acid sequence of the 70 Kd app.MW polypeptide has been reported. (Larocca, D. D., et al., *Cancer Research* 50:5925–5930 (1990)).

The 46 Kd app.MW glycoprotein and its immune complexes were detected in the serum of breast cancer patients using monoclonal antibodies against the glycoprotein. In addition, an increase in the levels of the 46 Kd app.MW glycoprotein in the patients' serum was also found to be associated with the advent of tumors. The structure of the 46 Kd app.MW glycoprotein and the areinc acid sequence of its polypeptide have been described. Also known are the anti-neoplastic and diagnostic use of this glycoprotein and its polypeptide as well as the corresponding DNA and RNA sequences of the polypeptide. (Larocca, D. D., et al., *Cancer Research* 51:4944–4998 (1991)), the text of which relating to the preparation and characterization of the 46 Kd app.MW glycoprotein is incorporated herein by reference.

The recognition of the importance of rotaviral infection, and of its epidermiological and economic consequences, has led to a substantial effort directed at its prevention by means of active immunization. However, current vaccine regimens have displayed poor efficacy.

Accordingly, there still is a need for a patent and effective treatment for rotaviral infection as well as its prophylaxis, substantially lacking detrimental side effects.

SUMMARY OF THE INVENTION

This invention relates to an anti-diarrheic product, comprising a foodstuff; and an anti-rotaviral infection effective amount of an agent selected from the group consisting of defatted human milk fat globules, the human milk mucin-70 Kd app.MW glycoprotein-46 Kd app.MW glycoprotein complex and a polypeptide comprising an amino acid sequence having the rotavirus-binding specificity of the 46 Kd app.MW HMFG glycoprotein.

Also part of this invention is an anti-diarrheic kit, comprising an anti-diarrheic composition comprising an anti-rotavirus agent selected from the group consisting of defatted human milk fat globules, skim milk, the human milk macromolecular fraction, whey, the human milk mucin 70-Kd app.MW glycoprotein-46 Kd app.MW glycoprotein complex, the 46 Kd app.MW glycoprotein, a polypeptide having the rotavirus-binding specificity of the 46 Kd app.MW HMFG glycoprotein, and mixtures thereof, alone or with a foodstuff and/or a pharmaceutically-acceptable carrier; and instructions for use of the kit.

This invention also relates to a method of retarding or countering rotavirus infection of a mammalian cell comprising contacting the cell with an anti-rotavirus infection effective amount of an agent selected from the group consisting of defatted human milk fat globules, skim milk, the human milk macromolecular fraction, whey, the human milk mucin 70 Kd app.MW glycoprotein-46 Kd app.MW glycoprotein complex, the 46 Kd app.MW glycoprotein, a polypeptide comprising an amino acid sequence having the rotavirus-binding specificity of the 46 Kd app.MW HMFG glycoprotein,and mixtures thereof.

This invention relates as well to a method of retarding or countering rotavirus infection of a subject's cells comprising administering to a subject at risk of or afflicted with a rotavirus infection an anti-rotavirus effective amount of an agent selected from the group consisting of defatted human milk fat globules, skim milk, the human milk macromolecular fraction, whey, the human milk mucin-70 Kd app.MW glycoprotein-46 Kd app.MW glycoprotein complex, the 46 Kd app.MW glycoprotein, a polypeptide comprising an amino acid sequence having the rotavirus-binding specificity of the 46 Kd app.MW HMFG glycoprotein, and mixtures thereof; and optionally, a pharmaceutically acceptable carrier, and/or a foodstuff.

Other objects, advantages and features of the present invention will become apparent to those skilled in the art from the following discussions.

DESCRIPTION OF THE PREFERRED EMBODIMENTS

This invention arose from a desire by the inventors to improve on prophylactic and therapeutic methods for treating diarrheal conditions associated with rotavirus infection in mammals, especially in humans. More particularly, the present invention provides an effective and potent agent for the treatment of gastroenteritis, and/or diarrhea, associated with a variety of conditions linked to rotavirus infection such as infantile gastroenteritis, and some types of diarrhea prevalent in nursing home and day care centers, and afflicting travelers and adults exposed to sick children and patients subjected to bone marrow transplant, persons with genetic immune deficiencies, those afflicted with acquired immune deficient diseases such as AIDS, and those who's immune systems are suppressed by drug administration and immunodeficient patients in general. In the general population, immunodeficient patients are particularly at risk for rotavirus infection, and where afflicted by it, are disadvantaged for mounting an immunological response to the virus.

This invention relies on the finding by the inventors that an agent associated with the human milk fat globule membrane, also present in skim milk, and the macromolecular fraction, has potent anti-rotaviral activity. The agent of this invention prevents and retards rotavirus infections and is effective in the treatment of diarrhea. Moreover, the agent of this invention is devoid of the drawbacks and side effects of other known therapies.

The method of the invention provides significant advantages over prior art methods for the treatment of diarrhea. The prior art has focussed on immunologic methods in the search for a therapy against diarrhea caused by infectious agents. Immunologically based methods, however, are ineffective for treating immunodeficient individuals who cannot muster the needed immunological response to fight the pressure of the virus. Preventative vaccine therapies, for example, fail to elicit an adequate immunological response in such individuals. In addition, vaccination against rotavirus infection is somewhat ineffective and impractical due to the existence of multiple strains of rotaviruses. Another method applied to the treatment of diarrhea by the prior art is the administration of anti-rotavirus serum. This is not a method of choice for treating gastrointestinal infections because of the limited availability of human immune sera, and the risks associated with using human products that may be a source of contamination with viruses such as the HIV and hepatitis viruses. Moreover, the substitution of animal sera for human sera would most likely elicit an immunological host rejection. Also, the utilization of a single serum will fail to provide complete protection against the multiple strains of rotaviruses. Furthermore, since large quantities of anti-rotaviral immune serum are needed for administration by mouth, the cost of producing these large quantities, thus, makes its mass production impractical.

The administration of the agent of this invention provides a highly effective anti-diarrheal effect without the drawbacks produced by other anti-viral agents such as α-interferon, ribonucleases, milk lipids and trypsin inhibitors.

One advantage afforded by the non-immunological milk agent of the invention over prior art products relies on the fact that the present agents bind to many strains of human rotaviruses as well as to rotaviruses of other species, e.g., mouse and simian, inhibiting viral replication of all strains tested, and prevent rotavirus-associated diarrhea in vivo. Thus, the agent of this invention provides protection for the treatment of, e.g., diarrhea caused by a wide range of rotavirus strains.

The components of human milk found to be effective in the treatment of gastroenteritis and diarrhea provided herein are different from the prior art agents discussed above. For example, the human fat globule membrane, the mucin complex and particularly the 46 Kd app.MW HMFG glycoprotein are readily distinguishable from other antiviral components of milk such as lipids, immunoglobulins and oligosaccharides. The defatted human milk fat globule membrane or the dHMFG macromolecular fraction, the whole milk mucin complex and the 46 Kd app.MW polypeptide were shown by the present inventors to physically bind to rotaviruses in the absence of immunoglobulins, lipids and oligosaccharides. The 46 Kd app.MW HFMG glycoprotein and the milk mucin complex are different from other polypeptides that are present in milk such as immunoglobulins, α-interferon, and the like.

The milk mucin complex is found in the acidic fractions of milk obtained by isoelectric focussing, and is easily separated by this method from immunoglobulins which are present in the basic fractions of milk. The milk mucin complex is, thus, also different from other antiviral agents present in milk.

Upon fractionation of the human milk fat globules, human milk globule membrane which is the globule's macromolecular component, and its acidic protein fraction retain The anti-rotaviral activity. When the defatted milk fat globule fraction is separated into different fractions, the anti-rotaviral activity of human milk remains mostly with the mucin complex. However, when the mucin complex is separated into its components the highest anti-rotavirus activity is found with 46 Kd app.MW glycoprotein. The 46 Kd app.MW glycoprotein preferentially binds simian and human rotaviruses when compared to the 70 Kd app.MW glycoprotein and the milk mucin depleted of the 46 Kd app.MW glycoprotein.

The human milk fat globules, the macromolecular fraction and the milk mucin complex which among other fractions contain the 46 Kd app.MW glycoprotein, and the 46 Kd app.MW glycoprotein, were all found by the present inventors to inhibit the infection by rotavirus of human and simian origin of cultured mammalian cells.

The mucin complex was shown by the present inventors to inhibit rotavirus infectivity with a 3000 fold greater specific activity than whole milk. These results are unexpected based on the ambiguous reports relating to the effect of human milk on rotavirus, and the reported inhibitory effects of other milk components on this virus.

The human 46 Kd app.MW glycoprotein was also shown by the inventors to bind to cells and cell extracts that are infected with a human rotavirus. Human strains of the virus, such as RRV, Wa, DS-1, P and ST-3, bind to the 46 Kd app.MW glycoprotein in essentially equivalent amounts thereto. Moreover, the inventors found that when sialic acid was removed from the 46 Kd app.MW glycoprotein, its binding to vital infected cells was substantially reduced. This reduction in binding of the 46 Kd app.MW polypeptide to rotavirus infected cells was found to be in the range of 30 to 60%. Thus, sialic acid may be required for the 46 Kd app.MW glycoprotein to retain its binding activity as well as anti-viral activity. Moreover, it is also possible that the anti-rotavirus activity of milk mucins from other sources lacking sialic acid may be enhanced by sialylation.

The inventors have also shown that the agent of this invention inhibits the in vitro infection of cells by rotaviruses as well as gastroenteritis induced by rotaviruses in an animal model. For instance, the administration of a murine rotavirus (EDIM) to suckling mice, caused a 100% incidence of diarrhea in the mice. However, the simultaneous administration of the virus and the human milk macromolecular or acidic glycoprotein fraction to the suckling mice, reduced the symptoms of diarrhea by 90%. In contradistinction, when a bovine milk-based formula or a control medium were administered instead, the rotavirus activity and the diarrheal symptoms remained undiminished.

The purification of the various components of the human milk fat globules may be conducted as described in the art, or by affinity purification as shown below. The agent of this invention is easily prepared for clinical use. Human breast milk may be readily fractionated by published methods into a macromolecular component comprising the fat globule membrane. This component is distinct from oligosaccharides, lipids, immunoglobulins and other small proteins contained in milk. Likewise, whole human milk, the macromolecular fraction, and the fat globules may be defatted to produce fat globule membranes.

The macromolecularfraction containing the milk mucin complex may be obtained by lipid extraction of fatty milk as described by Newburg, D. S., et al. (Newburg, D. S., et al, Pediatric Res. 31:22–28(1992)). The acidic glycoprotein fraction of milk may be obtained by isoelectric focusing as described by Yolken, R. M., et al. (Yolken, R. M., et al, J. Clin. Investigation 90:(1992)). Both these fractions have anti-rotavirus activities that are, respectively, 3 and 38 times greater than whole milk. The milk mucin complex may be affinity-purified in accordance with this invention or obtained as previously described (Ceriani et al., P.N.A.S. (USA) 74:582–589 (1977)). Natural skim milk may be prepared by centrifuging unfrozen fresh milk, and removing the cream fraction that contains intact milk fat globules. When fresh milk is frozen and thawed, especially several times, sonicated, allowed to stand for a period of time, or exposed to temperature, the fat globules are generally disrupted. When the fat layer is then separated from the remainder or "processed skim milk", it contains mainly the lipid fraction of the cream (butter consisting of mainly triglycerides), while the milk fat globule membranes, the 70 Kd app.MW and the 46 Kd app.MW.HMFG glycoproteins are now mainly in the "processed skim milk". However, the amount is greatly increased in the "processed skim milk", the amount increasing with more vigorously freezing and thawing and/or sonication. Both the natural and the processed skim milk have anti-rotavirus activity, with the latter evidencing higher activity. Curds and whey may be prepared as is known in the art, and will contain a certain proportion of the described components that have anti-rotavirus activity.

The milk mucin complex, in turn, may be further purified from the membranes using monoclonal antibodies as described herein, and the 46 Kd app.MW glycoprotein may be separated from the milk mucin complex. These components are separable by traditional chromatographic and/or electrophoretic methods. The presence and identities of the components of the human milk mucin complex are readily determined using available, specific monoctonal antibodies.

The gene encoding the 46 Kd app.MW polypeptide being available, the gene product and variations thereof may be prepared by recombinant technology and expressed in recombinant microorganisms as described by Larocca et al. (Larocca et al. Cancer Res. 51:4994–4998 (1991); Larocca et al. Hybridoma 11:191–201 (1992); Larroca, et.al., "Molecular Cloning and eExpression of Breast Mucin Associated Antigens"", in Breast Epit. helial Antigens, p. 36, Plenum Press, Ceriani, R. L., ed, N.Y., N.Y. (1991)). The amino acid sequence of the 46 Kd app.MW polypeptide is unrelated to any known immunoglobulin but was found to have significant homology to human epithelial cell proteins and the C1 C2 domains of the human clotting factors V and VIII, a mouse milk fat globule 67 Kd app.MW protein MFG-E8, discoidin of amoebae, and the A5 antigen of xenopus brain, among others.

Polypeptides having the iotavirus binding characteristics of the HMFG 46 Kd app.MW glycoprotein component of the mucin complex may be prepared synthetically, by sequencing or by adding a stop codon at a desired place in the DNA encoding the protein, by methods known in the art, or by purification from human milk of the 46 Kd app.MW glycoprotein and subsequent partial hydrolysis.

The synthetic polypeptide having the described characteristics may be prepared in different; lengths by alteration of the DNA sequence encoding it and adding a stop codon where desired, as is known in the art, and expression of the thus altered gene or fragments thereof. The gene encoding the 46 Kd app.MW polypeptide has been cloned and partially sequenced as discussed above.

The novel anti-rotaviral agent of this invention is suitable for use in most instances of rotavirus infection, and particularly in cases where other therapies are either ineffective or clinically contraindicated.

The agent of this invention exhibits additional advantages for the treatment of infants and children since, as already indicated, its components are normal constituents of human milk and the human diet. The present agent is thus unlikely to elicit toxic, immunological or allergic reactions in treated subjects. Because these agents are innocuous to the human body, the invention may be used without intervention of skilled medical personnel, for example, by adding it to foodstuffs, and the like, that are normally sold over-the-counter in convenience stores or as food supplements available in grocery stores. This is a particular advantage for treating travellers or populations in underdeveloped countries where medical services are in short supply.

The agent of this invention may be administered in combination with other treatments, such as immune therapy, particularly treatments that act by independent mechanisms, to thereby provide a multi-pronged attack on the virus. Other anti-rotaviral treatments may be combined with the present agent to provide a treatment compatible with other clinical needs of a patient, as well. For example, other milk components, such as oligosaccharides, α-interferon and trypsin inhibitors, known to have anti-microbial and anti-viral activity, may be combined with the present agent.

The inventors have found that components of human milk other than those encompassed by the invention failed to inhibit rotavirus infection in cell cultures. These agents, prepared by methods described in the art, include lipids, gangliosides, polar neutral glycolipids, non-polar glycolipids, triglycerides and fatty acids and neutral, acidic and total oligosaccharides.

The agent of the invention may be used alone, with a carrier or as an additive to a foodstuff, or in other compositions suitable for human consumption.

Thus, this invention provides an anti-diarrheic product, comprising a foodstuff; and an anti-rotaviral effective amount of an agent selected from the group consisting of defatted human milk fat globules, skim milk, the human milk macromolecular fraction, curd, whey, the human milk mucin-70 Kd app.MW glycoprotein-46 Kd app.MW glycoprotein complex, the 46 Kd app.MW HMFG glycoprotein, a polypeptide comprising an amino acid sequence having the rotavirus-binding characteristics of the 46 Kd app.MW HMFG glycoprotein, and mixtures thereof. Each agent may be used alone or combined with one or more of the agents provided herein, or further combined with a foodstuff or food supplement for self-administration.

The agent of this invention may also be provided in a composition with other components including, but not restricted to, vitamin supplements, mineral additives, other nutritional additives, buffers, salts, flavoring compounds, diluents, thickeners, emulsifiers, preservatives, and anti-oxidants, such as would be familiar to a person skilled in the art, as would the amounts they are added in to the composition.

The anti-diarrheic composition or product may also comprise a binder such as gum tragacanth, acacia, corn starch or gelatin, excipients such as dicalcium phosphate, anti-clumping agents such as corn starch, potato starch, alginic acid and the like, lubricants such as magnesium stearate, sweetening agents such as sucrose, lactose or saccharin, flavoring agents such as peppermint, orange, wintergreen or cherry flavoring as well as other known artificial and natural flavoring compounds. Sustained-release preparations and formulations are also within the confines of this invention, and may contain further ingredients as is know in the art.

A coated composition, or otherwise modified forms of the preparation are also contemplated herein such as coatings of shellac, gelatin, sugar and the like. Any material added to this product should be pharmaceutically-acceptable and substantially non-toxic in the amounts employed.

Other excipients may be added to the formulation such as those utilized for the production of ingestible tablets, troches, capsules, elixirs, suspensions, syrups and wafers, among others and the product may then be provided in these forms.

In one preferred embodiment, the product of the invention comprises the 46 Kd app.MW HMFG glycoprotein. The glycoprotein may be compounded with other anti-viral human milk components as well as other anti-viral and anti-microbial agents as indicated above. In another preferred embodiment, the product comprises the mucin complex or mixtures thereof.

The agent of this invention may be present in the anti-diarrheic product in an amount of about 0.01 to 99.9 wt % of the composition, and preferably about 0.1 to 20.0 wt %. However, other amounts of the agent may also be present in the product. The amount of the agent in the anti-diarrheic product may be varied, and/or the frequency of administration increased, depending on the severity of the infection, the general health and nutritional status of the subject, and whether or not other anti-rotavirus agents are being administered as well.

Foodstuffs suitable for use in the anti-diarrheic product of the invention are milk, juices, cereals, chewing gum, crackers, candies, meats, vegetables and fruits, blended or otherwise as baby food for example, and cookies, among others.

In another embodiment, the foodstuff of the product provided herein may be infant formula, milk, milk substitutes, baby foods, rehydration formula, and vitamin supplements, among others. This product may be specifically formulated for the palate of youngsters, when applied to the treatment of infants or small children.

This invention also provides an anti-diarrheic kit, comprising an anti-diarrheic composition comprising an agent selected from the group consisting of defatted human milk fat globules, skim milk, the human milk macromolecular fraction, curd, whey, the human milk mucin-70 Kd app .MW glycoprotein-46 Kd app.MW glycoprotein complex, the 46 Kd app.MW glycoprotein, a polypeptide comprising an amino acid sequence having the rotavirus-binding specificity of the 46 Kd app.MW HMFG glycoprotein, and mixtures thereof, and a pharmaceutically acceptable carrier; and instructions for use of the kit.

The anti-diarrheic composition of this kit may be administered in an amount of the anti-diarrheic product of about 0.1 to 1000 mg/kg body weight/day, and more preferably about 1 to 50 mglkg body weight/day. Other amounts, however, may also be administered. It is understood that the more active fractions, such as the 46 Kd app.MW glycoprotein may be administered at a lower dose, whereas the lesser active fractions such as the defatted milk fat globule may be administered at a higher dose. Other amounts may also be administered. This kit is formulated for the therapeutic treatment of subjects afflicted with or at risk of diarrheal conditions associated with rotaviral infection. The anti-diarrheic composition may also comprise vitamin supplements, mineral additives, other nutritional additives, salts, buffers, flavoring compounds, diluents, thickeners, emulsifiers, preservatives, and anti-oxidants, such as would be familiar to a person skilled in the art. Included within the invention, is an embodiment wherein the above anti-diarrheic compositions further comprise varying amounts of other components such as foodstuffs. Suitable are all kinds of foods including milk and milk supplements. The anti-diarrheic composition or the product of the invention may also be modified to include varying amounts of water and ingredients suitable to the clinical needs of the subject.

The anti-diarrheic composition may be mixed with a drink (liquid) or a foodstuff for self-administration. The composition may be added in an anti-rotaviral amount, and may be provided in bulk or in unit form.

This invention also provides an anti-diarrheic kit that comprises in separate, sterile containers a foodstuff; and an anti-rotaviral effective amount of an agent selected from the group consisting of defatted human milk fat globules, skim milk, the human milk macromolecular fraction, curd whey, the human milk mucin-70 Kd app.MW glycoprotein-46 Kd app.MW glycoprotein complex, the 46 Kd app.MW glycoprotein, a polypeptide comprising an amino acid sequence having the rotavirus-binding specificity of the 46 Kd app.MW HMFG glycoprotein and mixtures thereof, and optionally a pharmaceutically-acceptable carrier; and instructions for use of the kit.

For purposes of identification of the components, the apparent molecular weight (app.MW) of the glycoproteins of the invention may be determined by SDS-polyacrylamide gel electrophoresis using standard techniques described in the art. For example, defatted human milk fat globule membranes may be dissolved in a solution containing 1% sodium dodecyl chloride (SDC) and heated to disolve the glycoproteins, applied to a 3–30% polyacrylamide gel and electrophoresed with appropriate molecular weight standards run in a parallel lane, the apparent molecular weight (app.MW) of the mucin complex obtained is approximately 400,000 Kd app.MW or greater. The apparent molecular weights of other proteins may be determined in a similar manner. The 46 Kd and the 70 Kd app.MW glycoproteins associated with the milk mucin complex may also be identified by binding to the specific monoclonal antibodies Mc16 and Mc13, respectively (Larocca et al., Cancer Res. 51:4994 (1991); Peterson et al., Hybridoma 9:221–235 (1990), supra). The milk mucin, also referred to as breast mucin, may be identified in the complex by binding to the monoclonal antibody Mc5 described by Peterson, J. A., et al. (Peterson, J. A., et al., Hybridoma (1990), supra). If the defatted human milk fat globule is disolved in SDS under reducing conditions such as in the presence of 0.5% beta-mercaptoethanol, the 70 Kd app.MW glycoprotein runs as a doublet with an apparent molecular weight of 70. Kd, that may be further identified by binding to the monoclonal antibodies Mc13 and McR2. The 46 Kd app.MW glycoprotein under the same conditions, appears as a doublet with an apparent molecular weight of 46 Kd, as identified by binding to the monoclonal antibody Mc16 described by Larocca, et al. (Larocca et al., Cancer Res. 51:4994 (1991), supra). The milk mucin, under reducing conditions, is seen as a band of approximate 400,000 Kd apparent molecular weight and may be identified by binding to the monoclonal antibody Mc5 described by Peterson, J. A., et al. (Peterson, J., et al., Hybridoma (1990), supra). If the milk mucin, the 70 Kd app.MW glycoprotein, and the 46 Kd app.MW glycoprotein are treated to remove oligosaccharides, their apparent molecular weights, as determined by polyacrylamide gel electrophoresis, appear to decrease.

This invention additionally provides a method for retarding the onset of, or countering, rotavirus infection of a mammalian cell comprising contacting the cell in a nutrient medium with an anti-rotaviral infection effective amount of an agent selected from the group consisting of defatted human milk fat globules, skim milk, the human milk marcomoleculIar fraction, curd, whey, the human mucin-70 Kd app.MW glycoprotein-46 Kd app.MW glycoprotein complex, the 46 Kd app.MW glycoprotein, a polypeptide comprising an amino acid sequence having the rotavirus-binding specificity of the 46 Kd app.MW HMFG glycoprotein and mixtures thereof.

In one preferred embodiment of the invention, the anti-diarrheic agent comprises the 46 Kd app.MW HMFG glycoprotein in another embodiment, the agent comprises the mucin complex. Both of these agents may be administered alone and/or with defatted human milk fat globules, and/or whey, and/or curd, and/or skim milk, and/or the HMFG macromolecular component, and/or the 46 Kd app.MW HMFG glycoprotein, and/or a polypeptide having the rotavirus-binding specificity of the about 46 Kd app.MW HMFG glycoprotein and/or mixtures Thereof. Although the complete removal of glycosides from the mucin complex was shown to reduce the anti-rotavirus activity of the glycoprotein by at least 40–60%, agents having varying levels of glycosylation may be used, since they retain some activity.

This invention also provides a method of retarding the onset of, or countering, rotavirus infection of a subject's cells comprising administering to a subject at risk for, or suffering from, rotavirus infection an anti-rotavirus effective amount of the agent of this invention or mixtures thereof, or a composition comprising the agent of the invention and/or a pharmaceutically-acceptable carrier and/or a foodstuff and/or other additives as described above. The composition may incorporate other anti-vital or anti-microbial agents, as suitable for effective treatment of a rotavirus infection taking into account the age, general health, and nutritional status of the subject. Other compositions' of the agent of the invention and further comprising, e.g., the macromolecular fraction of the defatted milk fat globule membrane and the acidic fraction, are also contemplated herein.

Another aspect of this invention comprises a method of retarding the onset of, or countering, infantile gasteroenteritis associated with rotavirus infection comprising administering to an infant or child in need of the treatment a composition comprising an anti-rotavirus infection effective amount of an agent selected from the group consisting of defatted human milk fat globules, skim milk, the human milk macromolecular fraction, curd, whey, the human milk mucin-70 Kd app.MW glycoprotein-46 Kd app.MW glycoprotein complex, the 46 Kd app.MW glycoprotein, a polypeptide having the rotavirus-binding specificity of the 46 Kd app.MW HMFG glycoprotein, and mixtures thereof, and optionally a pharmaceutically-acceptable carrier and/or other agents and infant foodstuffs such as formula, milk, and the like, as described above. The above method may be used for the prophylaxis of the disease, particularly where demographic and public health information suggests significant risk of infection. When symptoms indicate the onset of infection, the method may also be applied therapeutically.

The agent of this invention may be present in the infant formula in an amount from 0.01 to 99.9 wt %, and more preferably about 0.1 to 2.0 wt % of the composition. Other amounts of the agent, however, may also be used. As this product is formulated for the prophylatic or therapeutic treatment of infants and children afflicted with or at risk of diarrheal conditions associated with rotaviral infection, the infant food product may include varying amounts of infant formula, juices, foods, milk or milk supplements, among others. This anti-diarrheic infant product may also include vitamin supplements, water, mineral and other nutritional additives, salts, buffers, flavoring compounds, diluents, thickeners, emulsifiers, preservatives, encapsulation agents, glycosidase inhibitors, protease inhibitors, and antioxidants, such as would be familiar to a person skilled in the art. The infant formula may also be modified to include varying amounts of water and other-solutes to meet other clinical needs of the infant or child. The human milk components of this invention being routinely consumed and consisting of biogical molecules, their administration will neither require clinical precautions nor medically trained personnel. Accordingly, the present products may be sold over the counter.

Also part of this invention is a method of retarding the onset of, or countering, diarrhea associated with rotavirus infection in a subject's cells comprising administering to a subject in need of such treatment a composition comprising an anti-rotavirus effective amount of an agent selected from the group consisting of defatted human milk fat globules, skim milk, the human milk macromolecular fraction, curd, whey, the human milk mucin-70 Kd app.MW glycoprotein-46 Kd app.MW glycoprotein complex, the 46 Kd app.MW glycoprotein, a polypeptide having the rotavirus-binding specificity of the 46 Kd app.MW HMFG glycoprotein and mixtures thereof, and optionally a pharmaceutically-acceptable carrier and/or a foodstuff. Because of minimal side effects associated with the agent used in this method, the agent may also be administered for diarrheal symptoms regardless of etiology to prevent secondary outbreaks associated with rotavirus infection.

This invention also provides a method of retarding the onset of, or countering, diarrhea associated with rotavirus infection in an immunodeficient subject comprising administering to an immunodeficient subject an anti-rotavirus effective amount of an agent selected from the group consisting of defatted human milk fat globules, the human milk macromolecular fraction, skim milk, curd, whey, the human milk mucin-70 Kd app.MW glycoprotein-46 Kd app.MW glycoprotein complex, the 46 Kd app.MW glycoprotein, a polypeptide having the antibody-binding specificity of the about 46 Kd app.MW HMFG glycoprotein, and mixtures thereof, optionally comprising a pharmaceutically acceptable carrier and/or foodstuffs as described above. Such immunodeficiencies may result from genetic dysfunction, organ transplant, disease induced conditions or as a consequence of medical treatment with drugs, among others.

Other agents that may be added to the composition for this particular application are bulking agents, carbon black, high fiber additives, encapsulation agents, protease inhibitors, glycosidase inhibitors, and carrier lipids, optionally micellar, among others. These may be present in amounts known in the art.

Specific applications of the above method are in cases of, e.g., transplants such as bone marrow, kidney, heart and other organ transplants. Transplant patients receiving immunosuppressant drugs may also benefit from this anti-diarrheic treatment.

The above preventative and therapeutic methods may be practiced by administering the agent provided herein as part of an anti-diarrheic composition also comprising a carrier or a product such as a foodstuff, as described above. Suitable foodstuffs are milk, juices, cereals, powdered grains, candies, confections, cookies, meats, vegetables and fruits, put through a blender or otherwise processed, and crackers, among others.

Having now generally described this invention, the same will be better understood by reference to certain specific examples, which are included herein for purposes of illustration only and are not intended to be limiting of the invention or any embodiment thereof, unless so specified.

EXAMPLES

Example 1: Source of Human Milk

Human milk was obtained from 30 healthy, lactating women donors to the Central Massachusetts Regional Milk Bank, Worcester, Mass. The donors were chosen to represent a wide range of maternal ages ranging from 20 to 37 years (average: 28±4 years), parity: 9 primiparous, 13 secundiparous, 5 tertiparous, 3 quadriparous with a 0 to 14 months lactation period (average:6.0±3.8 months postpartum). The milk was generally expressed in the morning by means of a mechanical pump, pooled and used to isolate the human milk components utilized below.

Example 2: Isolation of Oligosaccharide Components from Human Milk

The oligosaccharide fraction of human milk was prepared using the method of Newburg et al. (Newburg, D. S., Pickering, L. K., McCluer, R. H., and Cleary. T. G., "Fucosylated Oligosaccharides of Human Milk Protect Suckling Mice from-Heat-stable Enterotoxin of *Escherichia coil*"*J. Infect. Dis.* 162:1075–1080 (1990)).

Briefly, 1.5 l of human milk were centrifuged at 4° C. at 3,000×g for 1 hr to separate the cream from the skim milk. The cream was removed, and the skimmed milk was filtered through glass wool. The filtrate was then mixed with an equal volume of ice-cold acetone, stirred overnight at 4° C. and centrifuged at 3,000×g for 45 min to obtain a clear supernatant. The clear supernatant was concentrated by rotary evaporation at 40° C. to a volume of 300 ml and applied to a 1-L charcoal-Celite column (50% charcoal, 50% celite, Fischer Scientific, Boston, Mass.).

The column was extensively washed with distilled water and 5% aq. ethanol, and the oligosaccharide fraction was then eluted from the column with 50% aqueous ethanol. The eluate was passed through an AG 1-X2 anion-exchange resin (BioRad, Richmond, Calif.) to yield a neutral oligosaccharide fraction. The acidic oligosaccharides were eluted from the resin with 1M formic acid, and then dialyzed and lyophilized. All fractions were stored at −70° C. until used.

Example 3: Isolation of Lipid components from Human Milk

Whole human milk was extracted with 20 volumes of chloroform/methanol (2:1 ), filtered, and the filtrate evaporated. The lipids extracted in the chloroform phase were-then partitioned between hexane and 88% aqueous ethanol phases, free fatty acids being extracted in the hexane phase. Free fatty acids were removed from the hexane fraction by washing with methanolic ammonia, and recovered by acidifying and extracting the protonated fatty acids with hexane. The ethanol fraction was taken to dryness, and subjected to Folch partition with chloroform/methanol/water (8:4:3:v:v:v:) to obtain upper phase and lower phase lipid fractions.

The upper phase lipids were isolated on a sepralyte C 18 (40 nm) reverse-phase column (American Bioanalytical, Natick, Mass.), and then separated on DEAE Sepharose (Pharmacia, Uppsala, Sweden) into neutral glycolipids and anionic glycolipids referred to as the "neutral" and "ganglioside" fractions. The Folch lower phase lipids were separated on a Unisil silicic acid column (Clarkson Chemical, Williamsport, Pa. to isolate the lower phase glycolipid fraction.

Example 4: Isolation of Macromolecular Fraction From Human Milk

Whole human milk was frozen and thawed three times and subsequently sonicated for 20 minutes to disrupt the milk fat globules. The cream-derived lipids, mainly triglycerides, were separated from the milk by centrifugation at 3,000×g for 1 hour at 4° C. and removed by filtration through glass wool. The resulting skim milk was passed through a 300,000 Dalton molecular weight cut-off ultrafilter membranes. The retentate was washed three times with distilled water by diafiltration to remove small proteins. This retentate was then dialyzed to remove any residual molecules smaller than 40 Kd app.MW, and then lyophilized.

The specific activity was calculated as the amount of protein from whole pooled human milk representing the minimum inhibitory concentration ($MIC_{50}$) divided by the amount of protein from a purified fraction that represented the $MIC_{50}$.

The specific activity (Sa) of a given purified fraction was calculated from the following algebraic formula.

$$Sa_{(x)} = \frac{[WMP_{MIC50}]}{[x_{MIC50}]},$$

wherein the specific activity is obtained by dividing the concentration of protein from the original unprocessed whole pooled milk protein fraction that produces 50% inhibition [$WMP_{MIC50}$] by the concentration of protein from the purified fraction necessary to produce 50% inhibition in the same assay [$x_{MIC\ 50}$].

Example 5: Separation of Human Milk Components by Isoelectric Focussing

Isoelectric focussing was performed in a Rotofor apparatus (BioRad, Richmond, Calif.). The macromolecular fraction, prepared as described above, was made 1% with ampholytes, pH 3–10, in 50 ml distilled water, and was resolved into 20 fractions at 14 W for 4 hrs. The pH of each fraction was measured with a standard pH electrode, and each fraction was then dialyzed against distilled water, and lyophilized. Each fraction was then reconstituted with sterile phospate-buffered saline (PBS) such that each purified material was at the concentration at which it was found in the original pooled milk sample. The active fractions were pooled and refocussed as above, but over a pH gradient of 3.9 to 7.1 over 20 fractions.

The presence of glycoproteins immunologically related to human milk mucin: the 46 Kd app.MW glycoprotein, and the 70 Kd app.MW glycoprotein, in the highly focussed fractions was then determined as described by Peterson et al. (Peterson, J. A., et al., *Hybridoma* 9:221–235, (1990)). The presence of the glycoproteins was determined by depositing an aliquot of each fraction onto a well of a microtiter plate and adding to the plates, Mc5, a monoclonal antibody which specifically binds milk mucin, Mc13, a monoclonal antibody that specifically binds to the 70 Kd app.MW glycoprotein and, Mc16, a monoclonal antibody that binds specifically to the 46 Kd app. Mw glycoprotein. Where present, the glycoproteins bound to the wall and their binding to the antibody was quantitated by a subsequent reaction with peroxidase labeled anti-mouse IgG, and o-phenylene diamine $H_2O_2$ substrate. The mucin-related glycoprotein activity was expressed as the optical density at 450 nm generated by reaction in the wells coated with the milk fractions minus the optical density generated by reaction in a control well without milk components. The fractions binding the antibody were pooled and designated as acidic glycoprotein.

The presence of IgG and secretory IgA immunoglobulins in the fractions obtained by isoelectric focussing was tested by the solid phase enzyme immunoassay procedure of Yolken et al modified as described below. (Yolken, R. H., et al., *J. Pediatr.* 93:916–921 (1978)).

Briefly, the Yolken et al assay comprises binding immunoglobulins to the surface of a solid support, reacting the immunoglobulins with enzyme- or otherwise-labeled anti-immunoglobulin antibodies, and reacting, e.g., the bound enzyme with a color-changing substrate, so that a change in the wavelength in the color-producing region permits the quantitation of the specific immunoglobulin present in the initial sample.

The presence of trypsin inhibitory activity in the fractions was also tested using a benzoyl-DL-arginine-p-nitroanilide (BAPNA) substrate in accordance with Vonderfecht et al. (Vonderfecht, S. L., et al, *J. Clin. Invest.* 82:2011–2016 (1988)).

Example 6: Isolation of Human Milk Mucin Complex

The human milk mucin complex present in delipidated or defatted human milk fat globules (Peterson, J. A. et al., *Hybridoma* 9:221–235. (1990)) was isolated by affinity chromatography using the Mc5 monoclonal antibody that recognizes the tandem repeat region of the human milk mucin. (Peterson, J. A., et al., in *Breast Epithelial Antigens: Molecular Biology to Clinical Applications*. R. L. Ceriani, ed., Plenum Publications, New York, pp. 55–68 (1991)). The Mc5 monoclonal antibody was conjugated with cyanogen bromide activated Sepharose-4B beads (Pharmacia, Uppsala, Sweden) at a ratio of 1 mg of IgG/ml swollen beads. The antibody coated beads were washed and suspended in PBS containing 0.3%. Triton X-100, 10% bovine serum and 0.1% sodium azide. Delipidated human milk fat globule was dissolved in the same buffer, sonicated, and incubated with antibody coated beads overnight at 4° C. The beads were alternately washed 3 times with 0.1M Na acetate, 1M NaCl, pH 4.0, and 0.1M Tris buffer, pH 8.0, and twice with PBS containing 0.3% Triton X-100. The bound mucin complex was eluted with 3M sodium isocyanate and concentrated by dialysis.

Example 7: Separation of Human Milk Mucin Components

The milk mucin, and the 46 Kd app.MW and 70 Kd app.MW glycoprotein components of the milk mucin complex were separated by fractionation of defatted human milk fat globule under reducing conditions (0.5% β-mercaptoethanol), followed by electrophoresis in a 3%–15% SDS polyacrylamide gel. One lane was stained with Coomassie blue to identify the components while the remainder of the gel was frozen. Bands containing the reduced human milk mucin of approximately 400 Kd app.MW, the 70 Kd app.MW glycoprotein component, and the 46 Kd app.MW glycoprotein component were excised from the gel, separately homogenized, placed in dialysis bags and eluted from the gel bands by electrophoresis in the presence of 0.5% β-mercaptoethanol and 2M dithiothreitol.

The eluted proteins were separated from the gel by centrifugation. Each protein was characterized by its binding to specific monoclonal antibodies (Mc5 for milk mucin, and Mc13 for the 70 Kd app.MW glycoprotein and and Mc16 for the 46 Kd app.MW glycoprotein) (Peterson et al (1990), supra).

Example 8: Desialylation of Human Mucin Components

Sialic acid was removed in one set of samples from the components purified in Example 7 by chemical hydrolysis using a previously described method (Gibbons, R. A., *Biochem. J.* 89:380–391 (1963); Gyorky, G.et al., *Can. J. Biochem.* 43:1807–1811 (1965); Jourdian, G. W., et al., *J. Biol Chem.* 246:430–435 (1971)).

Briefly, samples containing 1 to 10 mg of human milk glycoproteins purified as described above, were suspended in 1 ml 0.08N $H_2SO_4$, and digested for 1 hour at 80° C. After rapid cooling on ice, the samples were neutralized with 100 μl of 0.8M NaOH, exhaustively dialyzed and lyophilized.

The glycosidic linkages of the sialic acid residues of glycoproteins are uniquely sensitive to mild acid hydrolysis. The specificity of a chemical hydrolysis of glycosidic linkages is dependent upon the reaction conditions which are employed. Since 0.1N hydrochloric acid results in the hydrolysis of 20% of acylneuraminic acids, dilute sulfuric acid hydrolysis of sialic acid is preferred. The release of sialic acids from human serum and brain was optimal with 0.1N sulfuric acid at 80° C. for 1 hour, depending on the concentration of sialic acid in the sample (Suennerholm, L., *Acta Chem. Scand.* 12:547–584 (1958)). Thus, the conditions for acid hydrolysis (0.08N $H_2SO_4$, 80° C., 60 minutes) used effect complete release of sialic acid, a partial release of approximately 3% of the fucose and negligible release of other sugars. (Gyorky, G. et al., *Can J. Biochem.* 43:1807–1811 (1965).).

Example 9: Effect of Desialylation on Binding of the 46Kd app.MW HMFG Glycoprotein to Rotavirus The binding inhibition assay was conducted as shown in Example 12. The separation of sialic acid by hydrolysis from the 46 Kd app.MW glycoprotein reduced its ability for binding to various rotavirus strains. Since the rotaviruses do not hemagglutinate erythrocytes or bind to other sialic acid-containing compounds, it is thus possible that the linkages involved in the viral binding to the apparent molecular weight 46 Kd app.MW glycoprotein are different from those present on erythrocytes and other sialic acid-containing compounds.

Another possibility is that the rotavirus does not bind directly to a sialic acid-containing portion of the target molecule, and that the removal of sialic acid results in a conformational alteration of the 46 Kd app.MW binding epitope. It is unlikely that the chemical hydrolysis of the 46 Kd app.MW glycoprotein eliminates the reactivity of the MC16 monoclonal antibody to the resulting glycoprotein since this antibody recognizes a peptide domain of the glyceprotein (Peterson, J. A., et al. *Hybridoma* 9:221–235 (1990)). Furthermore, the monoclonal antibody was demonstrated to still bind to the 46 Kd app.MW glycoprotein following chemical desialylation.

Example 10: Isolation of Various Strains of Rotavirus

The rhesus rotavirus (RRV) strain MMU 18006, the simian rotavirus strain SA-11, the mouse rotavirus strain (EDIM) and the human rotavirus strains Wa, DS-1, P, and ST3 were propagated in MA-104 cells using the method described by Yolken, R. H., et al. (Yolken, R. H., et al., "Sialic Acid Glycoproteins Inhibit the in Vitro and In Vivo Replication of Rotaviruses", *J. Clin. Invest.* 79:148–154 (1987)).

The serotype of the neutralization protein VP7 was determined for all strains. The simian strains were shown to belong to serotype 3, whereas the human strains Wa, Ds-1, P and ST3 belong to serotypes 1, 2, 3, and 4, respectively (Moshino, Y., et al., *J. Infect, Dis.* 149:694–702 (1984)).

Example 11: Binding of Various Rotavirus Strains to Mucin

Briefly, the above viruses were diluted in PBS to concentrations of approximately $10^3$ pfu/ml and immobilized onto wells of microtiter plates coated with methylated bovine serum albumin as described by Ceriani et al. (Ceriani, R. L. in:*Monoclonal Antibodies and Functional Cell Lines. Progress and Applications*, Bechtol, K. B., McKern, T. J. and Kennett, R., eds., Plenum Press, New York. pp. 398–402 (1984)).

The control wells were coated with an equivalent concentration of uninfected MA-104 cells under identical conditions. After washing the wells with PBS-Triton-X100, the viruses and the controls were reacted with the mucin components at a concentration of 0.5 μg/well.

The binding of the mucin components to the virus and the uninfected control cells was determined by reaction with monoclonal antibodies Mc5, Mc13, and Mcl 6 that are specific for mucin, the 70 Kd app.MW glycoprotein, and the 46 Kd app.MW glycoprotein components of the native mucin complex, respectively. After washing with. PBS-Triton X-100, $^{125}I$ labelled anti-murine IgG was added. (Peterson et al (1990), supra). The binding was quantitated by measuring the $^{122}I$- labeled anti-murine IgG attached to well-bound monoclonal antibodies.

Each sample was measured in quadruplicate and a binding ratio was calculated for each component by dividing the average number of counts generated in the virus-coated well by the average number of counts generated in the control wells with uninfected cells.

Example 12: Inhibition by Human Milk Mucin Fractions of Rotavirus Infection

The human milk fractions prepared as described above were diluted to varying concentrations in Eagle's Modified Essential Medium (EMEM) containing 0.5 to 1 μg/ml porcine trypsin and approximately 100 pfu of the MMU rotavirus strain. The cells were allowed to adsorb the virus-milk factor mixture for 1 hr at 37° C. The cell monolayers were then washed and covered with an overlay of agarose containing 0.5 μg/ml trypsin plus the anti-viral milk factor at the same concentration used for the adsorption step. The samples were incubated for approximately 5 days at 37° C., a second agarose overlay containing neutral red dye was added, and the stained plaques counted.

The percentage inhibition was calculated for each concentration of all milk components used as follows.

Percentage inhibition=$100 \times (1-(P_s/P_c))$, wherein $P_f$ is the number of plaques generated in cells infected with virus incubated with the milk factor, and $P_c$ is the number of plaques generated in the virus infected cells in the absence of added milk fractions.

Each fraction was initially tested at a concentration equivalent to that in which it is found in the human milk pool. The samples which demonstrated inhibition were then retested at 10-fold dilutions. The minimum inhibitory concentration ($MIC_{50}$) for each fraction was calculated by interpolating the minimum concentration required for the 50% inhibition of plaque generation.

Example 13: Inhibition by Milk Mucin of In Vivo Rotavirus Infection

A murine rotavirus (EDIM) strain responsible for epizootic diarrhea in infant mice was purified by ultracentrifugation through CsCl. The ability of the macromolecular fraction and the acidic glycoprotein fraction prepared as described in Examples 4 and 5 above, respectively, to prevent diarrhea associated with EDIM in suckling mice was tested. The EDIM rotavirus was separately incubated at a concentration of 10 $ID_{100}$/ml with the different milk fractions and with control preparations at a concentration of 100 µg/ml.

The control preparations contained bovine milk-based infants' formula (Similac, Ross Laboratories), or minimum essential media.

Following incubation for 30 minutes at 37° C., 100 µl of the milk-virus mixture were fed to individual mice in separate litters of suckling mice. To minimize variations among litters, the suckling mice were pooled and then randomly divided among the dams immediately prior to inoculation. The suckling mice remained with these dams throughout the course of the study. The development of diarrhea was observed for 3–5 days following infection with the virus. The suckling mice continued to receive milk from their mothers during the course of the study.

The macromolecular fraction of human milk totally prevented the development of rotavirus gastroenteritis in the animal model. Furthermore, feeding the milk acidic glycoprotein component along with rotavirus resulted in >90% protection against symptomatic gastroenteritis. On the other hand, neither infant formula based on cow's milk or tissue culture media afforded any measurable protection against symptomatic infection.

Example 14: Inhibition of Rotavirus Infection in Suckling Mice by Milk Components 0.1 ml aliquots of the EDIM murine rotavirus containing $x10^6$ pfu/ml were separately incubated with individual milk components or control solutions and fed to suckling mice. The macromolecular and acidic glycoprotein human milk components were tested at concentrations of 100µg/ml and the bovine milk formula and the tissue culture media were tested without dilution. The following exposure to the rotavirus development of diarrhea in the animals was observed for 3–5 days.

The macromolecular fraction of human milk prevented the development of rotavirus-induced diarrhea by nearly 100% in suckling mice. When fed to the suckling mide infected with rotavirus the acidic glycoprotein component of human milk resulted in greater than 90% protection against diarrheal symptoms.

Neither an infant formula based on cow's milk nor tissue culture media by themselves provided a significant degree of protection against symptomatic rotavirus infection.

Example 15: Determination of Milk Components Having Anti-Rotavirus Infection Activity The oligosaccharide, lipid, and macromolecular protein components of human milk were fractionated and reconstituted to a concentration ten-fold greater than in the original milk as described by Newburg, D. S., et al. (Newburg, D. S., et al., Pediatric Res. 31:22–28 (1992)). The ability of each of the fractions to inhibit the replication of the SA-11 rotavirus strains in tissue culture was then tested at ten-fold their concentration found in human milk, and at logarithmic dilutions, e.g., 1:10, 1:100, 1:1,000, 1:10,000, etc.

The lipids extracted from whole human milk were fractionated into ganglioside, polar neutral glycolipid, non-polar glycolipid, triglyceride and fatty acid fractions as described by Newburg, D. S., et al. (Newburg, D. S., et al. (1992), supra)). None of the lipid components of the milk displayed significant anti-rotavirus activity at any concentration.

In addition, the milk oligosaccharides were separated into neutral and acidic oligosaccharide fractions, both of which aisc failed to show anti-rotaviral activity.

The macromolecular fraction (>300 Kd app.MW MW) was shown to inhibit the replication of the prototype SA-11 rotavirus strain (VP7 serotype 3) with a minimum inhibitory concentration of approximately 100 µg/ml. This is a 3-fold increase in activity when compared to the original whole human milk pool.

The macromolecular fraction of human milk was further fractionated by high-resolution preparative isoelectric focusing as described by Newburg et al. (Newburg, D. S., et al., *Pediatr. Res.* 31:22–28 (1992)). The inhibitory activity of the rotavirus was confined to fractions with a pi of 4.0 to 4.6. These fractions did not contain immunoglobulins detectable by solid phase immunoassay or protease inhibitory activity measured by reaction with trypsin and benzoyl-DL-arginine-p-nitroanilide (BAPNA) substrate.

These acidic fractions with anti-rotaviral activity also reacted with monoclonal antibodies directed at the human milk mucin complex. The acidic fractions with anti-rotaviral activity were pooled and designated as the acidic-glycoprotein fraction of human milk. This acidic glycoprotein fraction inhibited the replication of the SA-11 rotavirus at a concentration of 8 µg/ml (1:500 dilution from its original concentration in milk). This represents a 38-fold increase in specific activity.

Example 16: Inhibition of Rotavirus Infection by the Purified Mucin Complex

The active human milk mucin complex of the invention was affinity purified from defatted human milk fat globule utilizing the monoclonal antibody Mc5 as described above in Example 6. The affinity-purified milk mucin complex inhibited the infection of the simian SA-11 virus in MA-104 cells at a concentration of 0.1 µg/ml (approximately $2\times10^{-10}$ mol/l, based on a molecular weight of 500,000). This is a 3,000-fold increase in specific activity over whole milk. Thus, the affinity purified complex shows extremely potent activity to block rotavirus infection. Furthermore, the complex binds directly to rotavirus, as measured using the solid phase binding assay of Example 11.

Example 17: Inhibition of Human Rotavirus Infection by Purified Mucin Complex - Effect of Sialic Acid The mucin complex was deglycosylated by treatment with hydrogen fluoride for 3 hours at room temperature as described by Mort and Lainport (Mort and Lamport. *Anal Biochem.* 82:238–309 (1977)). These conditions result in the hydrolysis of most glycosidic bonds as well as a substantial reduction in the inhibition of rotavirus activity by the complex. No significant rotavirus inhibition was measurable at 10 µg/ml deglycosylated mucin, the highest concentration tested.

Various human rotavirus strains were incubated with the human milk macromolecular glycoprotein fraction at a concentration of 250 µl/ml and propagated in MA-104 cells as described herein. The macromolecular glycoprotein fraction of human milk, at a concentration of 250 µl/ml, inhibited approximately 55–80% the in vitro replication of 4 human strains of rotavirus (WA, OS-1, P, St-3).

The viruses were also incubated with the desialylated macromolecular fraction of the milk mucin complex, followed by propagation in MA-104 cells. For all 4 human virus strains, the inhibition of rotavirus infection was reduced (WA, DS-1) or abolished (Pt, St-3) by the chemical desialylation of the milk glycoprotein.

Example 18: Specific Binding of Rotavirus to the 46 Kd app.MW HMFG Glycoprotein

The native, affinity purified milk mucin complex was found to bind specifically to cells infected with the simian SA-11 rotavirus.

The milk mucin complex was fractionated under reducing conditions, which resulted in the dissociation of the complex in its components. Following fractionation, the isolated milk mucin components were exposed to rotavirus and to uninfected cells (control) bound to microtiter plates. The reduced 46 Kd app.MW glycoprotein of the milk mucin complex separated by gel electrophoresis retained substantial viral binding activity. The rotavirus specifically bound the 46 Kd app.MW glycoprotein component of the mucin complex whereas no significant binding was found to occur with the 70 Kd app.MW glycoprotein component or with the reduced residual macromolecular mucin in the absence of the 46 Kd app.MW or the 70 Kd app.MW glycoprotein components.

The 46 Kd app.MW component bound to the simian rotavirus strain RRV (VP7 serotype 3) and to human rotavirus strains Wa, DS-1, P, and ST3 (VP7 serotypes 1, 2, 3, and 4, respectively). The 46 Kd app.MW HMFG glycoprotein bound to each of the human strains with approximately equal avidity. The binding of the 46 Kd app.MW HMFG glycoprotein to the human vital strains did not differ significantly from its binding to the simian strain.

The hydrolysis of sialic acid in the 46 Kd app.MW glycoprotein resulted in a substantial decrease in the binding of the 46 Kd app.MW glycoprotein to the rhesus rotavirus and the other human rotavirus strains (all p<0.01; 2 tailed t-test).

The invention now being fully described, it will be apparent to one of ordinary skill in the art that many changes and modifications can be made thereto without departing from the spirit or scope of the invention as set forth herein.

What is claimed as novel in Letters Patent of the United States is:

1. An anti-viral composition comprising
    an agent selected from the group consisting of defatted human milk fat globule, the haman milk macromolecular fraction, the human milk mucin-70 Kd apparent MW HMFG glycoprotein:46 Kd apparent MW HMFG glycoprotein complex, the 46 Kd apparent MW HMFG glycoprotein, a polypeptide comprising an amino acid sequence having the rotavirus-binding specificity of the 46 Kd apparent MW HMFG glycoprotein, deglycosylated proteins thereof, mixtures thereof, and mixtures thereof with human skim milk, curd, or whey; and
    a therapeutic agent, or mixtures thereof.

2. The composition of claim 1, further comprising an additive selected from the group consisting of coatings, sustained release additives, carrier lipids, lubricants, bulking agents, carbon black, high fiber additives, encapsulation agents, nutritional additives, buffers, salts, flavoring agents, diluents, thickeners, emulsifiers, preservatives, antioxidants, binders, excipients, anti-clumping agents, sweeteners, and mixtures thereof.

3. The composition of claim 1, further comprising a pharmaceutically acceptable carrier.

4. The composition of claim 1, further comprising a foodstuff, wherein the agent is dispersed.

5. The composition of claim 4, wherein the foodstuff comprises milk, whey, curd, infant formula, juices, cereals, candy, chewing gum, cookies, crackers, vegetables, meats, fruits, or mixtures thereof.

6. The composition of claim 1, wherein the agent comprises a polypeptide comprising an amino acid sequence having the rotavirus-binding specificity of the 46 Kd apparent MW HMFG glycoprotein, deglycosylated proteins thereof, or mixtures thereof.

7. The product of claim 6, wherein the agent comprises the 46 Kd apparent MW HMFG glycoprotein, deglycosylated proteins thereof, or mixtures thereof.

8. The composition of claim 1, wherein the agent is present in amount of 0.01 to 99.9 wt %.

9. An anti-vital kit comprising, in separate sterile containers,
    the agent of the composition of claim 1;
    a therapeutic agent, and-mixtures thereof; and
    instructions for use of the kit.

10. A method of retarding or treating rotavirus infection in a subject, comprising administering to the subject a composition comprising an anti-rotavirus effective amount of an agent selected from the group consisting of defatted human milk fat globule, the human milk macromolecular fraction, the human milk mucin-70 Kd apparent MW glycoprotein-46 Kd apparent MW glycoprotein complex, the 46 Kd apparent MW glycoprotein, a polypeptide comprising an amino acid sequence having the rotavirus-binding specificity of the 46 Kd apparent MW HMFG glycoprotein, deglycosylated proteins thereof, mixtures thereof, and mixtures thereof with human skim milk, curd, or whey.

11. The method of claim 10, wherein the agent comprises a polypeptide comprising an amino acid sequence having the rotavirus-binding specificity of the 46 Kd apparent MW HMFG glycoprotein, deglycosylated proteins thereof, or mixtures thereof.

12. The method of claim 11, wherein the agent comprises the 46 Kd apparent MW HMFG glycoprotein, deglycosylated proteins thereof, or mixtures thereof.

13. The method of claim 12, wherein the agent comprises synthetic 46 Kd apparent MW HMFG glycoprotein, deglycosylated proteins thereof, or mixtures thereof.

14. The method of claim 10, wherein the agent is administered to the subject in an amount of 0.1 to 1000 mg/kg body weight/day.

15. The method of claim 10, wherein the composition further comprises a carrier.

16. The method of claim 15, wherein the carrier comprises a pharmaceutically acceptable carrier.

17. The method of claim 10, wherein the carrier comprises a foodstuff, in which the agent is dispersed.

18. The method of claim 17, wherein the foodstuff comprises milk, whey, curd, infant formula, juices, cereals, candy, chewing gum, cookies, crackers, vegetables, meats, fruits, or mixtures thereof.

19. The method of claim 10, wherein the agent is present in the composition in an amount of 0.01 to 99.9 wt %.

20. The method of claim 10, wherein the subject is a normal subject.

21. The method of claim 10, wherein the subject is a transplant subject.

22. The method of claim 21, wherein the transplant subject is a bone marrow transplant subject.

23. The method of claim 10, wherein the subject is an immunodeficient subject.

24. The method of claim 23, wherein the immunodeficient subject is afflicted with a genetic immune deficiency.

25. The method of claim 23, wherein the immunodeficient subject is afflicted with an acquired immune deficiency.

26. The method of claim 23, wherein the immunodeficient subject's immune system is depressed or suppressed by drag administration.

27. The method of claim 10, wherein the subject is an elderly subject.

28. The method of claim 10, wherein the subject is an infant or a child.

29. The method of claim 10, further comprising administering to the subject an anti-viral agent.

30. The method of claim 29, wherein the anti-viral agent is selected from the group consisting of α-interferon, ribonucleases, oligosaccharides, anti-rotaviral immunoglobulins, trypsin .inhibitors, anti-rotaviral serum, anti-rotavirus vaccines, and combinations thereof.

31. The method of claim 10, wherein the composition further comprises an additive selected from the group consisting of therapeutic agents, coatings, sustained release additives, carrier lipids, bulking agents, carbon black, high fiber additives, encapsulation agents, nutritional additives, buffers, salts, flavoring agents, diluents, thickeners, emulsifiers, preservatives, anti-oxidants, binders, excipients, anti-clumping agents, lubricants, sweeteners, and mixtures thereof.

32. The method of claim 10, wherein the subject is an animal.

33. The method of claim 32, wherein the subject is a human.

34. A method of retarding or treating diarrhea associated with rotavirus infection in a subject comprising administering to the subject a composition comprising anti-diarrhea effective amount of an agent selected from the group consisting of defatted human milk fat globule, the human milk macromolecular fraction, the human milk mucin-70 Kd apparent MW HMFG glycoprotein-46 Kd apparent MW HMFG glycoprotein complex, the 46 Kd apparent MW HMFG glycoprotein, a polypeptide comprising an amino acid sequence having the rotavirus-binding specificity of the 46 Kd apparent MW HMFG glycoprotein, deglycosylated proteins thereof, mixtures thereof, and mixtures thereof with human skim milk, curd, or whey.

35. A method of retarding or treating infantile gastroenteritis associated with rotavirus infection comprising administering to an infant in need of the treatment a composition comprising an anti-infantile gastroenteritis effective amount of an agent selected from the group consisting of defatted human milk fat globule, the human milk macromolecular fraction, the human milk mucin-70 Kd apparent MW glycoprotein-46 Kd apparent MW glycoprotein complex, the 46 Kd apparent MW glycoprotein, a polypeptide comprising an amino acid sequence having the rotavirus-binding specificity of the 46 Kd apparent MW HMFG glycoprotein, deglycosylated products thereof, mixtures thereof, and mixtures thereof with human skim milk, curd, or whey.

36. A method of retarding or treating diarrhea associated with rotavirus infection comprising administering to a subject in need of the treatment a composition comprising an anti-diarrhea effective amount of an agent selected from the group consisting of defatted human milk fat globule, the human milk macromolecular fraction, the human milk mucin-70 Kd apparent MW glycoprotein-46 Kd apparent MW glycoprotein complex, the 46 Kd apparent MW glycoprotein, a polypeptide comprising in amino acid sequence having the rotavirus-binding specificity of the 46 Kd apparent MW HMFG glycoprotein, deglycosylated products thereof, mixtures thereof, and mixtures thereof with human skim milk, curd, or whey.

37. A method of retarding or treating diarrhea associated with rotavirus infection in an immunodeficient subject comprising administering to an immunodeficient subject in need of the treatment a composition comprising an anti-diarrhea effective amount of an agent selected from the group consisting of defatted human milk fat globule, the human milk macromolecular fraction, the human milk mucin-70 Kd apparent MW glycoprotein-46 Kd apparent MW glycoprotein complex, the 46 Kd apparent MW glycoprotein, a polypeptide comprising an amino acid sequence having the rotavirus-binding specificity of the 46 Kd apparent MW HMFG glycoprotein, deglycosylated products thereof, mixtures thereof, and mixtures thereof with human skim milk, curd, or whey.

38. The method of claim 25, wherein the subject afflicted with an acquired immune deficiency is an HIV+ subject.

39. The method of claim 23, wherein the immunodeficient subject is afflicted by a disease-induced immunodeficiency.

40. The method of claim 21, wherein the transplant patient is further administered immunosuppressant therapy.

41. The method of claim 10, further comprising administering to the subject an agent selected from the group consisting of immunosuppressant drugs, α-interferon, ribonucleases, vitamins, minerals, milk lipids, protease inhibitors, glycosidase inhibitors, and mixtures thereof.

42. A method of retarding or treating rotavirus infection in a subject, comprising administering to the subject the composition of claim 1, in an amount effective to deliver an anti-rotavirus effective amount of the agent.

43. A method of retarding or treating diarrhea associated with rotavirus infection in a subject comprising administering to the subject the composition of claim 1, in an amount effective to deliver an anti-diarrhea effective amount of the agent.

44. A method of retarding or treating infantile gastroenteritis associated with rotavirus infection comprising administering to an infant in need of the treatment the composition of claim 1, in an amount effective to deliver an anti-infantile gastro enteritis effective amount of the agent.

45. A method of retarding or treating diarrhea associated with rotavirus infection comprising administering to a subject in need of the treatment the composition of claim 1, in an amount effective to deliver an anti-diarrhea effective amount of the agent.

46. A method of retarding or treating diarrhea associated with rotavirus infection in an immunodeficient subject comprising administering to an immunodeficient subject in need of the treatment the composition of claim 1, in an amount effective to deliver an anti-diarrhea effective amount of the agent.

47. The composition of claim 1, wherein the therapeutic agent is selected from the group consisting vitamins, minerals, immunosuppressant drugs, α-interferon, ribonucleases, milk lipids, protease inhibitors, glycosidase inhibitors, lubricants, and mixtures thereof.

48. The composition of claim 1, in dehydrated form.

49. The composition of claim 1, wherein the active ingredient is provided in coated form.

50. The composition of claim 1, provided in coated form.

51. The composition of claim 1, for use in the form of a tablet, troche, capsule, elixir, suspension, syrup, or wafer.

52. The composition of claim 1, in the form of a tablet, troche, capsule, elixir, suspension, syrup, or wafer.

53. The composition of claim 1, in the form of a sustained release formulation.

54. The composition of claim 1, in self-administrable form.

55. The composition of claim 1, in unit form.

56. The composition of claim 1, in bulk form.

57. A food supplement, comprising the composition of claim 1, wherein the additive comprises vitamins and minerals.

58. An anti-microbial product, comprising the composition of claim 1, wherein the additive comprises at least one therapeutic agent.

59. A product, comprising a baby or infant foodstuff; and the composition of claim 1.

60. The product of claim 59, wherein the foodstuff comprises formula.

61. The product of claim 60, in rehydratable form.

62. The kit of claim 9, further comprising an additive selected from the group consisting of coatings, sustained release additives, carrier lipids, bulking agents, carbon black, high fiber additives, encapsulation agents, nutritional additives, buffers, salts, flavoring agents, diluents, thickeners, emulsifiers, preservatives, anti-oxidants, binders, excipients, anti-clumping agents, lubricants, sweeteners, mixtures thereof, and carriers.

63. The kit of claim 9, wherein the therapeutic agent is selected from the group consisting of vitamins and minerals.

* * * * *